(12) United States Patent
Beck et al.

(10) Patent No.: US 11,202,718 B2
(45) Date of Patent: Dec. 21, 2021

(54) CLAMPING BAND

(71) Applicant: BAUERFEIND AG, Zeulenroda-Triebes (DE)

(72) Inventors: André Beck, Stadtroda (DE); Frank Albert, Langenwolschendorf (DE); Hans B. Bauerfeind, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 100 days.

(21) Appl. No.: 16/348,150

(22) PCT Filed: Nov. 8, 2017

(86) PCT No.: PCT/EP2017/078556
§ 371 (c)(1),
(2) Date: May 8, 2019

(87) PCT Pub. No.: WO2018/087122
PCT Pub. Date: May 17, 2018

(65) Prior Publication Data
US 2019/0350736 A1    Nov. 21, 2019

(30) Foreign Application Priority Data
Nov. 11, 2016   (DE) .................... 10 2016 121 657.7

(51) Int. Cl.
  *A61F 5/01*   (2006.01)
  *A61F 5/02*   (2006.01)
(52) U.S. Cl.
  CPC .......... *A61F 5/0106* (2013.01); *A61F 5/0118* (2013.01); *A61F 5/026* (2013.01)

(58) Field of Classification Search
  CPC ...... A61F 5/0106; A61F 5/0118; A61F 5/026; A61F 5/32; A61F 5/02; A61F 5/00;
  (Continued)

(56) References Cited

U.S. PATENT DOCUMENTS

2008/0146981 A1\* 6/2008 Greenwald ............... A61F 5/01
                                                                                602/13
2009/0082707 A1    3/2009 Rumsey
(Continued)

FOREIGN PATENT DOCUMENTS

CN          103083841 A     5/2013
DE       102009049526 A1    5/2010
(Continued)

OTHER PUBLICATIONS

"International Preliminary Report on Patentability" from PCT/EP2017/078556 dated Mar. 8, 2019, English translation of the Written Opinion Form PCT/IPEA/409.
(Continued)

*Primary Examiner* — Alireza Nia
*Assistant Examiner* — Daniel A Miller
(74) *Attorney, Agent, or Firm* — Dentons Durham Jones Pinegar; Sarah W. Matthews

(57) ABSTRACT

The present invention relates to a tensioning strap comprising a strap-shaped base body that is compressible and/or extensible in the longitudinal direction, and comprising at least one pull cable, wherein the pull cable runs at least once along the longitudinal direction of the base body, and wherein the pull cable is deflected at at least one end of the base body. The present invention also relates to various possible applications of the tensioning strap according to the invention—in particular, in the field of medical aids, orthopedic aids, or sports aids.

18 Claims, 6 Drawing Sheets

(58) Field of Classification Search
CPC .................. A61F 5/0127; A61F 5/013; A61F 2005/0169; A61F 2005/0167; A61H 39/04; A61H 7/00; A61H 11/00; A61H 1/00
USPC ............... 602/60, 19, 41, 20, 23, 26, 28
See application file for complete search history.

(56) References Cited

U.S. PATENT DOCUMENTS

| | | | |
|---|---|---|---|
| 2009/0118655 A1 | 5/2009 | Wang | |
| 2014/0221893 A1* | 8/2014 | Modglin | A61F 5/026 602/19 |
| 2014/0276318 A1* | 9/2014 | Faux | A61F 5/0109 602/28 |
| 2015/0150705 A1* | 6/2015 | Capra | A61F 5/0123 602/6 |
| 2016/0095734 A1* | 4/2016 | Sigurdsson | A61F 5/0109 602/26 |
| 2016/0310310 A1* | 10/2016 | White | A61F 5/02 |
| 2019/0053930 A1* | 2/2019 | Beck | A61F 5/013 |

FOREIGN PATENT DOCUMENTS

| | | |
|---|---|---|
| DE | 102010035309 A1 | 2/2012 |
| DE | 102010054579 A1 | 6/2012 |
| DE | 102012009214 A1 | 11/2013 |
| DE | 102014012654 A1 | 2/2016 |
| DE | 202016100799 U1 | 3/2016 |
| EP | 2651349 A1 | 4/2017 |
| GB | 429059 A | 5/1935 |
| WO | WO2014074645 A2 | 5/2014 |

OTHER PUBLICATIONS

Chinese National Intellectual Property Administration, Office Action, Chinese Application No. 201780069505.5, dated Oct. 12, 2020.

* cited by examiner

CLAMPING BAND

CROSS-REFERENCE TO RELATED APPLICATIONS

This application is a 371 of international application PCT/EP2017/078556, filed 8 Nov. 2017, which claims priority to DE 102016121657.7, filed 11 Nov. 2016, each of which is incorporated herein by reference.

FIELD OF INVENTION

The present invention relates to a tensioning strap comprising a strap-shaped base body, which is compressible and/or extensible in the longitudinal direction, and comprising at least one pull cable, wherein the pull cable runs at least once—preferably, at least twice—along the longitudinal direction of the base body, and wherein the pull cable can preferably be deflected at at least one end of the base body. The present invention also relates to various possible applications of the tensioning strap according to the invention—in particular, in the field of medical aids, orthopedic aids, or sports aids.

BACKGROUND

Belts and straps are often used as traction belts or tension belts in orthopedic or medical aids, or sports aids. For example, DE 10 2010 054 579 A1 describes an orthosis for cushioning or limiting the joint movement of an extremity joint, in which a cuff and an abutment to the cuff are connected in a force-fitting manner by means of at least one traction strap.

Meanwhile, the traction belts or traction straps used until now have been replaced by cables—in particular, thin cords (that is, cables with a small diameter); for example, a joint movement is guided by a cord system of such an orthosis or bandage.

Unfortunately, in addition to their advantages (for example, small installation space, high flexibility, low loss of force due to friction), cords have the decisive disadvantage of cutting into skin, given their small diameter. In order to reduce the incision, the area under the cord must be enlarged. The current state of the art provides for static plate or shell elements that, when the cord is shortened, slide over each other, and as they are described in DE 20 2016 100 799 A1. However, such elements are very limited in their adjustment track. The plate or shell elements must also be assembled from many individual parts in an elaborate manufacturing and assembly process, and secured against not being recognized by each other. Due to this construction, the assemblies are quite stiff and inflexible. The cord guidance through tunnel straps can lead to the folding of the tunnel straps due to the material buckling during tensioning. This can impair wearing comfort.

Nevertheless, such orthopedic aids, medical aids, or sports aids—in particular, orthoses or bandages—shall become increasingly slimmer, lighter, and thinner in the future, with the effectiveness remaining at least the same.

SUMMARY

Disclosed herein is a tensioning strap or clamping band which may comprise a strap-shaped base body with a longitudinal direction, wherein the base body is compressible and/or extensible in the longitudinal direction, and comprising at least one pull cable, wherein the pull cable runs at least once along the longitudinal direction of the base body, wherein the base body is designed as at least one of a netted strap and a mesh strap. In some configurations, the base body of the tensioning strap is compressible in the longitudinal direction. The tensioning strap may be suitable for tensioning a belt around a part of the body. In some configurations, the tensioning strap may extend at least twice along the longitudinal direction of the base body.

The pull cable may be deflected at at least one end of the base body. The tensioning strap may be a component of at least one of an orthopedic aid, a medical aid, and/or a sports aid. The pull cable of the tensioning strap or clamping band may be formed as a pulley block. In some configurations, the pull cable may be movably mounted in the base body. The pull cable may be fastened at one end of the base body.

In some configurations, the tensioning strap or clamping band may have at least one of the netted strap and mesh strap formed of plastic. At least one of the netted strap and mesh strap may comprise a multiple number of recesses. In some configurations, a respective end element, which has a fastening device and/or a deflecting device for the pull cable may be assigned to the base body at its longitudinal direction ends. A roll-up element for tensioning and rolling up the pull cable may be assigned to the base body at one longitudinal direction end.

According to another aspect, the tensioning strap may be used as an orthopedic aid, medical aid, or sports aid comprising a tensioning strap as described here. The orthopedic aid may be an orthosis. The tensioning strap of the orthopedic aid may be designed to encompass a part of the body, which permits a circular closure of the tensioning strap.

In another configuration, the orthosis for cushioning or limiting the joint movement of an extremity joint, may have a cuff encompassing the extremity below the joint, which cuff is coupled to an abutment that can be applied to the extremity above the joint, wherein the pull cable extends from the abutment to the cuff and is connected in a force-fitting manner to the abutment and cuff, wherein the cuff is assigned to the base body of the tensioning strap and the tensioning strap is formed as a pressure initiation section of the cuff, and wherein the pull cable is formed in such a manner that, in the applied state of the orthosis, it can be tensioned by the joint movement of the extremity, in order to thereby, via the tensioning strap, exert compression on an underlying soft-tissue region of the extremity, in order to cushion or limit the joint movement. The pull cable may be tensioned in the area of the abutment by a roll-up element.

BRIEF DESCRIPTION OF THE SEVERAL VIEWS OF THE DRAWINGS

The present invention is explained with reference to the exemplary figures below, without the object of the figures being understood as limiting.

The following is shown.

DETAILED DESCRIPTION

Figure 1:
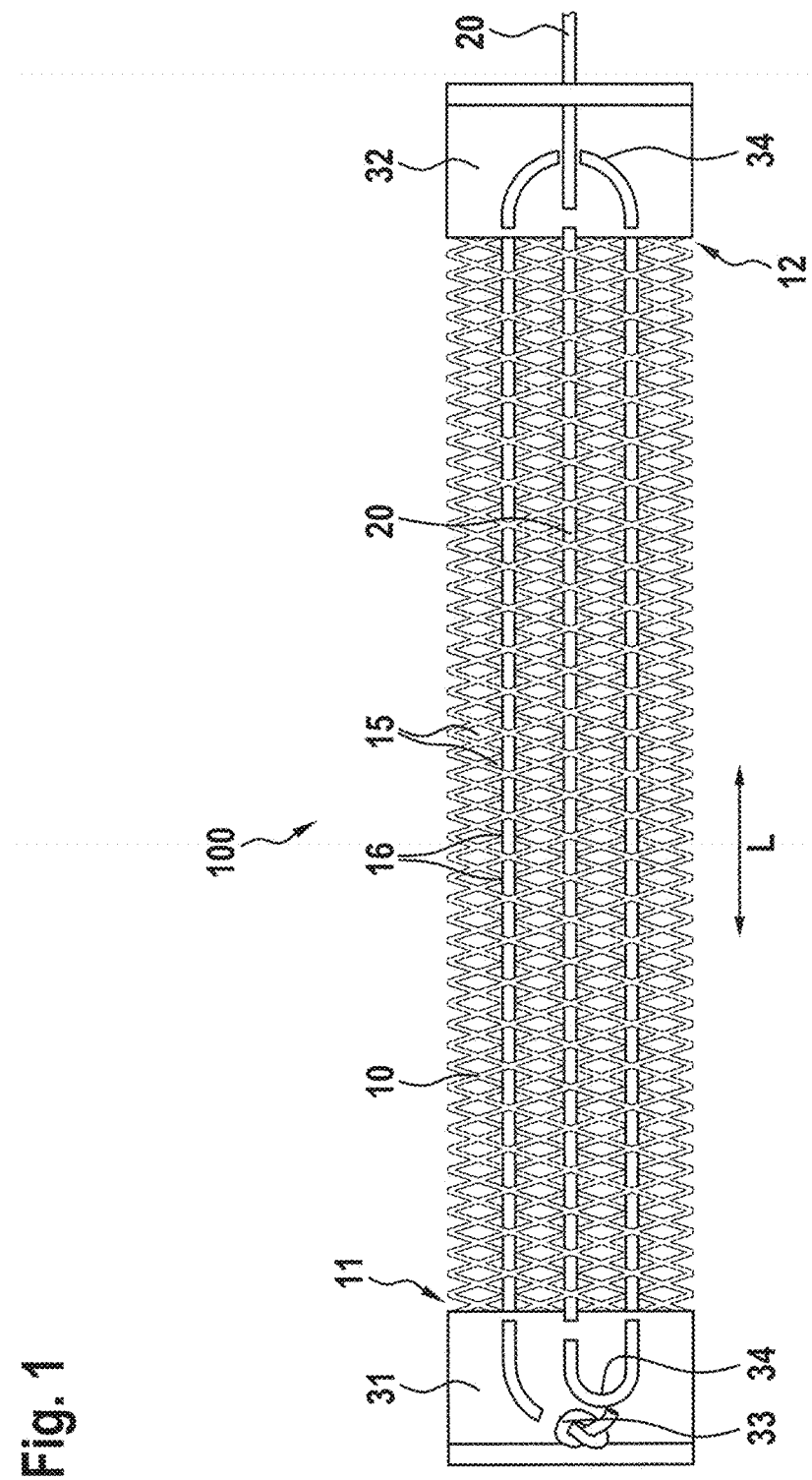
FIG. 1 a tensioning strap according to the invention in a relaxed state.

The present disclosure is therefore based upon the technical problem of mitigating the disadvantages arising from the prior art. In particular, devices and elements that make it possible to improve the straps or cables used—in particular, in orthopedic or medical aids or sports aids, in particular, orthoses or bandages—are to be provided, wherein, in particular, the force of the cables is distributed so that the cables do not cut into the skin of the wearer. An additional problem underlying the present disclosure is the provision of a device that does not cause the skin tissue underneath to be moved or clamped in the event of a change in circumference or length of an aforementioned aid.

The present disclosure solves the underlying technical problem, in particular, by means of a tensioning strap according to claim 1 and by means of an orthopedic aid, medical aid, or sports aid according to claim 12.

The present disclosure solves underlying the technical problem, in particular, by means of a tensioning strap, comprising a strap-shaped base body with a longitudinal direction, wherein the base body is compressible and/or extensible in the longitudinal direction, and comprising at least one pull cable, wherein the pull cable runs at least once—preferably, at least twice—along the longitudinal direction of the base body. The pull cable is preferably deflected at at least one end of the base body—in particular, if it runs at least twice along the longitudinal direction of the base body. In particular, if the pull cable simply runs along the longitudinal direction of the base body, the pull cable is preferably connected (in particular, firmly connected) to this at one end of the base body.

Such a tensioning strap allows a positive-locking, flexible application to any substrate in an advantageous manner, due to its constructive properties (that is, shape, structure, and material properties). By dispensing with fixed static elements (such as internal guide elements) in the longitudinal or transverse direction, the tensioning strap exhibits flexible behavior in all axes and in torsion. Thus, it is possible, in an advantageous manner, to flexibly dissipate the forces that arise over the contact surfaces.

It has been shown that the tensioning straps according to the present disclosure enable the use of a cable—in particular, a cord—in a medical aid, orthopedic aid, or sports aid—in particular, in an orthosis or a bandage—without the cables—in particular, cords—cutting into the skin of the wearer of the aid. This is achieved, in particular, by the fact that the basic element covers a large area of the wearer's skin and prevents a direct contact of the cable with the skin, and thus an incision in the skin, through the large-area distribution of force.

In some configurations, the pull cable is mounted movably in the base body.

In some configurations, the pull cable runs two to five times along the longitudinal direction of the base body—in particular, two to four times along the longitudinal direction of the base body.

The pull cable may be designed as a pulley block if it runs at least twice along the longitudinal direction of the base body. In some configurations, the pull cable is formed as a pulley block. Preferably, the pull cable is fastened to one end of the base body. The design as a pulley block has the advantage that the expenditure of force required to contract the base body is less.

The pulley block system enables an axial flow of force along the neutral fiber, which forms the ideal bending line. The position in which the tensioning strap is located does not matter. A neutral fiber, also known as a zero line, is the term used in strength theory to describe the fiber or layer of a cross-section of an elongated body whose length does not change with twisting or bending. At that point, the stress does not cause any tensile, compressive, or shear stress; the neutral fiber is force-free. It runs through the geometric center of gravity of the cross-sectional area of the bar when this is straight.

In one configuration, by means of a double deflection, the force introduced by the cord is transmitted evenly on the body, even with different layers of the tensioning strap.

In some configurations, the pull cable runs three times along the longitudinal direction of the base body.

The tensioning strap according to the invention can be used in a wide variety of fields—in particular, orthopedic aids, medical aids, or sports aids. The tensioning strap may be a component of an orthopedic aid, a medical aid, or a sports aid.

The tensioning strap may be used to tension a belt around a part of the body—for example, a leg, an arm, or the upper body. However, the tensioning strap can also be used as a belt that is tensioned around a part of the body. The tensioning strap can also be used to tension other elements, such as partial areas of an orthosis or a bandage. The tensioning strap can, in an advantageous manner, not only replace a belt or a cord, but can also be attached to a belt in order to be able to tension or relax the belt.

The base body may be designed as a netted strap or a mesh strap. Such a netted strap or mesh strap has the additional advantage that it is particularly light and breathable—especially compared to a conventional traction belt.

The netted strap or the mesh strap preferably has a diamond-shaped structure. This may be particularly easy to compress.

Thus, in accordance with the present disclosure, the base body is preferably a mesh-like or net-like base body. Due to the mesh structure, the base body can be contracted more advantageously by tensioning the tensioning strap, and the tensioning strap can be released to allow the base body to be pulled apart.

In some configurations, the pull cable runs at least once through the netted strap or mesh strap. For example, the netted strap or mesh strap can, due to interleaves, form a channel in which the pull cable runs. In particular, it can be provided that the netted strap or mesh strap feature interleaves partly on the top side and partly on the bottom side—in particular, that the interleaves alternate on the top side and on the bottom side of the netted strap or mesh strap. This holds the movable pull cable in the netted strap or mesh strap. Alternatively, the netted strap or mesh strap can have holes in its longitudinal direction—for example, bores through which the pull cable is pulled.

The netted strap or mesh strap may be made of a flexible material—in particular, plastic.

The netted strap or mesh strap may be made of a flexible material—in particular, plastic—which has a multiple number of recesses.

The netted strap or mesh strap may be made of a flexible material—in particular, plastic—which has a multiple number of diamond-shaped recesses. The person skilled in the art is familiar with suitable flexible materials, including rubber-like plastics. A material with low friction properties may be used for the base body.

The base body can also consist of several different materials. For example, a 2-component technology, with which the base body is produced by injection molding, is possible. Therefore, materials such as plastics with a low coefficient of friction can be used, advantageously, at all points where the cord experiences high friction due to deflection, while other plastics with different properties can be used in other areas. The material of the base body can also be elastic or essentially inelastic.

In one embodiment, an end element is assigned to the base body at one of its longitudinal ends, which end element has a fastening device for the pull cable.

In one embodiment, an end element, which has a fastening device and/or a deflecting device for the pull cable, is assigned to the base body at each of its longitudinal direction ends. Thus, the pull cable can be fastened to at least one end element and can be deflected at least by the other end element, such that it runs in the base body and is indirectly connected to the base body, but is not immediately and directly fastened to the base body. The end elements can be connected to a belt in a fixed or connectable manner. The end elements can also be used as fastening means for the tensioning strap on an orthopedic aid, medical aid, or sports aid.

In an alternative embodiment, an element for tensioning and rolling up the pull cable is assigned to the base body at one longitudinal end. The element for tensioning and rolling up can, for example, be located on or in an end element, or attached to the end element. The person skilled in the art is familiar with suitable elements for tensioning and rolling up a pull cable, such as rotary knobs with a lockable spool.

In another embodiment, the pull cable is a cord, i.e., a cable with a thin diameter. The person skilled in the art is familiar with suitable cords and suitable materials for such cords.

The pull cable can consist of a thread, a cable, or the like. The pull cable transmits the tensile forces that arise in the transverse direction of the base body and converts them into surface pressure. In an advantageous manner, this enables precise contact even on highly-contoured surfaces, without impairing the function.

The present disclosure also applies to products that have a tensioning strap according to the invention. In particular, the invention relates to an orthopedic aid, a medical aid, or a sports aid, comprising a tensioning strap according to the present disclosure.

The tensioning strap may be, in some configurations, fastened in or to an orthopedic or medical aid or sports aid—in particular, in or to an orthosis or a bandage, in particular, a component of an orthopedic or medical aid or sports aid—in particular, an orthosis or a bandage.

The orthopedic aid may be an orthosis.

The orthosis can be, for example, an arm orthosis, a leg orthosis, or a spinal orthosis. In some configurations, it may be an orthosis for extremities. For example, it can be an orthosis that performs a supporting or motion-gliding function—in particular, an orthosis for cushioning or limiting the flexion or extension of an extremity joint, such as an elbow joint or knee joint. Such an orthosis is known, for example, from DE 10 2010 054 579 A1. A person skilled in the art can easily replace the traction straps shown there with cables—in particular, cords—and the pressure initiation section shown there with a tensioning strap according to the invention. Therefore, the present disclosure also relates to a correspondingly-modified orthosis as described in DE 10 2010 054 579 A1. Therefore, the subject matter of DE 10 2010 054 579 A1 is incorporated into the present disclosure.

An orthopedic aid, medical aid, or sports aid in which the tensioning strap is designed to encompass a part of the body, which permits a circular closure of the tensioning strap, may be preferred in some configurations.

One configuration of an orthosis according to the present disclosure may comprise an orthosis for cushioning or limiting the joint movement of an extremity joint, having a cuff encompassing the extremity below the joint, which cuff is coupled to an abutment that can be applied to the extremity above the joint, wherein the pull cable extends from the abutment to the cuff and is connected in a force-fitting manner to the abutment and cuff, wherein the cuff is assigned to the base body of the tensioning strap and the tensioning strap is formed as a pressure initiation section of the cuff, and wherein the pull cable is designed in such a manner that, in the applied state of the orthosis, it can be tensioned by the joint movement of the extremity, in order to thereby, via the tensioning strap, exert compression on a thereunder-lying soft tissue region of the extremity, in order to cushion or limit the joint movement.

The pull cable may be tensioned in the area of the abutment by a roll-up element.

In one configuration, the pull cable of the orthosis runs twice and crossed-over from the abutment to the pressure initiation section of the cuff, and is deflected at the pressure initiation section by the deflection element according to the invention.

In one configuration, the abutment is formed as a second cuff.

According to another configuration, the first cuff and/or the second cuff are flexible cuff belts, which can preferably be opened and put on by means of a Velcro closure.

According to another configuration, the cuff and abutment are upgraded to a textile knitted fabric.

According to another configuration, the pull cable can be tensioned in the area of the abutment by means of a roll-up element. In this configuration, the pull cable is therefore tensioned by means of the roll-up element, by which the base body of the tensioning strap is contracted in the area of the first cuff, such that the tensioning strap encompasses the extremity more strongly.

According to yet another configuration, the tensioning strap is not used in a circular encompassing manner; rather, it spans only a partial section of a circular path or a straight line. The section of the circular path or straight line not spanned by the tensioning strap can be designed to be either elastic or inelastic.

For example, the tensioning strap can be used to apply pressure to only a part of the area.

In an additional embodiment, the tensioning strap can also be linear instead of circular. This embodiment can be used, for example, with a spinal orthosis—especially with the belts of a spinal orthosis. With such use, the tensioning strap can be interrupted by an area of an elastic or inelastic knitted fabric.

Other embodiments also result from the subclaims.

The present invention is explained in more detail and by way of example on the basis of the figures, wherein the figures and the corresponding explanation are not to be understood as restrictive.

FIG. 1 shows a tensioning strap (100) according to the invention in a relaxed state. The tensioning strap (100) has a strap-shaped base body (10) in the form of a netted strap or a mesh strap. A pull cable (20) runs in the strip-shaped base body (10), wherein the pull cable (20) is guided three times along the longitudinal direction (L) of the strip-shaped base body (10). The strap-shaped base body (10) consists of a flexible material and, as a netted strap or a mesh strap, has a multiple number of diamond-shaped recesses (15). In addition, the strip-shaped base body (10) has notches (16) in which the pull cable (20) is movably mounted. The notches (16) are located alternately on the top side and bottom side of the base body (10), whereby the pull cable (20) remains assigned to the base body (10), but nevertheless can be moved and pulled in the longitudinal direction (L). An end element (31, 32) is assigned to each of the two longitudinal direction ends (11, 12) of the strip-shaped base body (10). At the end element (31), the pull cable (20) is indirectly connected via a fastening device (33) to the strip-shaped base body (10). The fastening element is here formed as a bar (33), through which the pull cable (20) is pulled and secured by a knot. At the opposite end element (32), the pull cable (20) is not fastened; rather, it emerges from the end element (32) and can there be pulled.

Both end elements (31, 32) have deflection devices (34) with which the pull cable (20) is deflected, such that, as a pulley block, it passes through the strip-shaped base body (10) three times. The deflecting devices (34) can be formed, for example, as trench-like indentations in the end elements (31, 32), in which the pull cable (20) runs and which predetermine the running direction of the pull cable (20).

If the pull cable (20) is pulled at the protruding end in the area of the end element (32), the strap-shaped base body (10) contracts in the longitudinal direction (11) in the shape of an accordion, and the tensioning strap (100) is tensioned.

Figure 2:
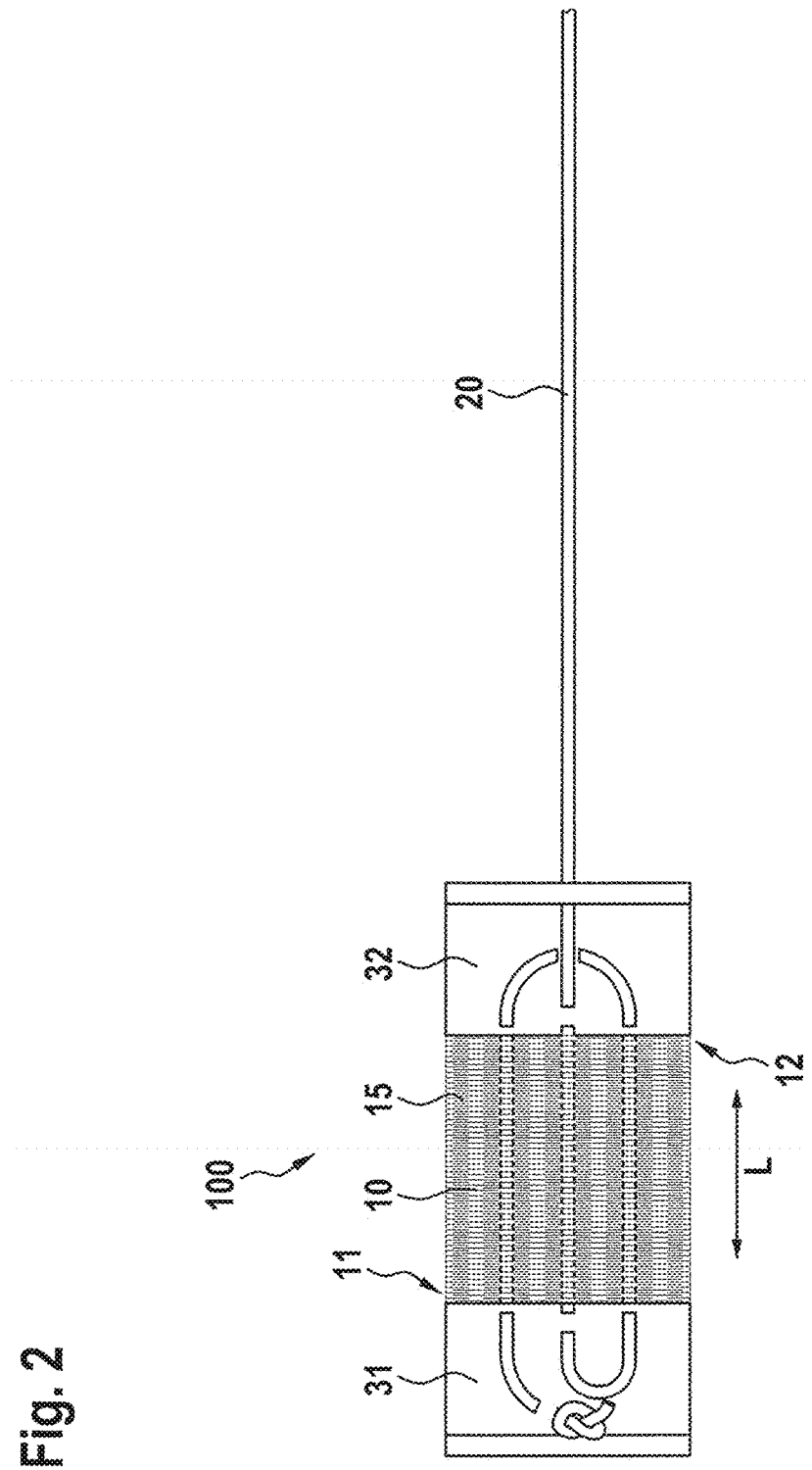
FIG. 2 the tensioning strap according to the invention of FIG. 1 in a tensioned state.

FIG. 2 shows the tensioning strap (100) in a tensioned state. The pull cable (20) has been pulled out, such that the strip-shaped base body (10) has contracted in the longitudinal direction (L), whereby the diamond-shaped recesses (15) are reduced in size, and the two longitudinal ends (11, 12) are contracted with the end elements (31, 32) and lie closer to one another.

Figure 3:
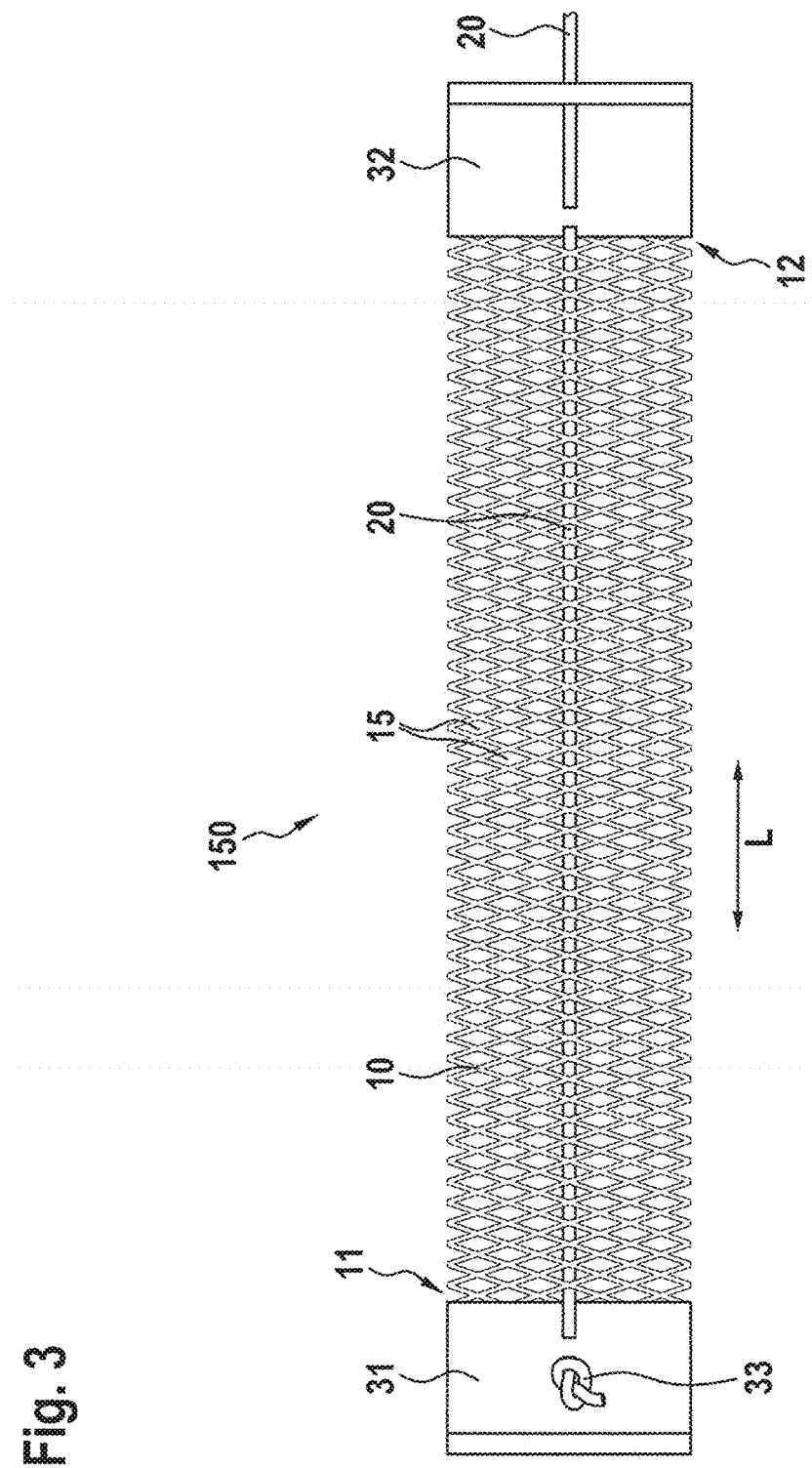
FIG. 3 an alternative embodiment of the tensioning strap according to the invention.

FIG. 3 shows an alternative embodiment of the tensioning strap (150) according to the invention. In this embodiment, the pull cable (20) is guided once through the strip-shaped base body (10) in the longitudinal direction (L). Moreover, the pull cable (20) is not inserted into indentations of the strap-shaped base body (10); rather, it is pulled through holes in the strap-shaped base body (10). No deflection elements are necessary, due to the simple tension guidance. However, the two longitudinal direction ends (11, 12) with the end elements (31, 32) there can be seen once again, wherein the pull cable (20) is again fastened to the end element (31) via a bar and a knot as a fastening device (33). The function of the tensioning strap (150) shown is the same as that of the tensioning strap (100) from FIG. 1, wherein, in the present embodiment, there is no pulley effect.

Figure 4:
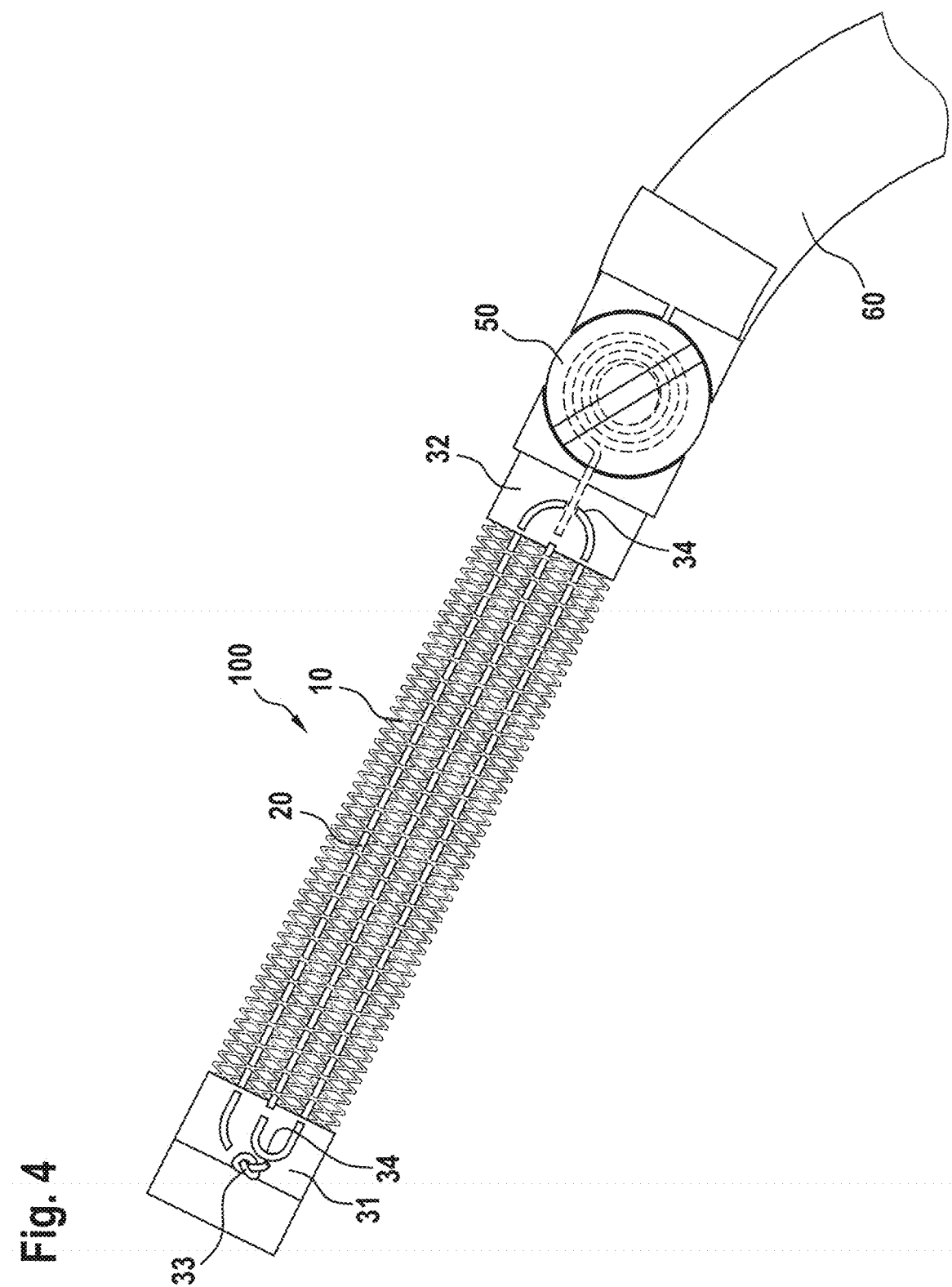
FIG. 4 a tensioning strap according to the invention with a roll-up element and a belt.

FIG. 4 shows the tensioning strap according to the invention (100) from FIG. 1, with a roll-up element (50) and a belt (60) fastened to it. The tensioning strap (100) once again has the elements already shown in FIG. 1—specifically, the strap-shaped base body (10) through which the pull cable (20) runs—wherein the pull cable (20) is fastened to one end element (31) via a bar/knot combination (33) and is deflected once at each of the two end elements (31, 32) by means of a deflecting device (34). A roll-up element (50) in the form of a rotatable spool is fastened to the end element (32) from which the pull cable (20) emerges, with which the pull cable (20) can be rolled up for tensioning the tensioning element (100). A belt (60) is fastened to the other side of the roll-up element (50). The tensioning element (100) can be regarded as a section of the belt (60), such that the total belt length is shortened by rolling up the pull cable (20) onto the roll-up element (50) and the resulting contraction of the strip-shaped base body (10).

Figure 5:
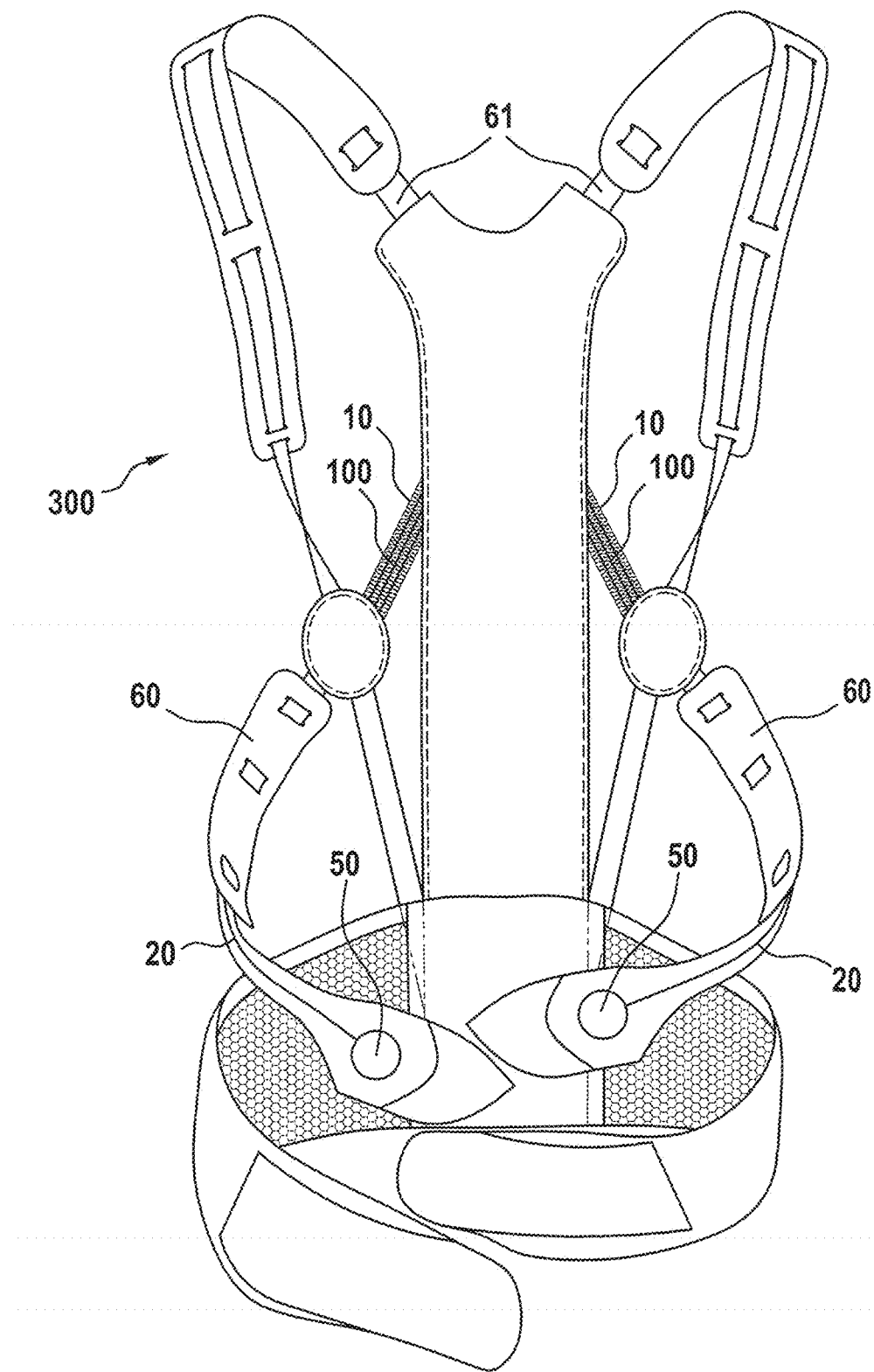
FIG. 5 an orthopedic aid with a tensioning strap according to the invention.
Figure 6:
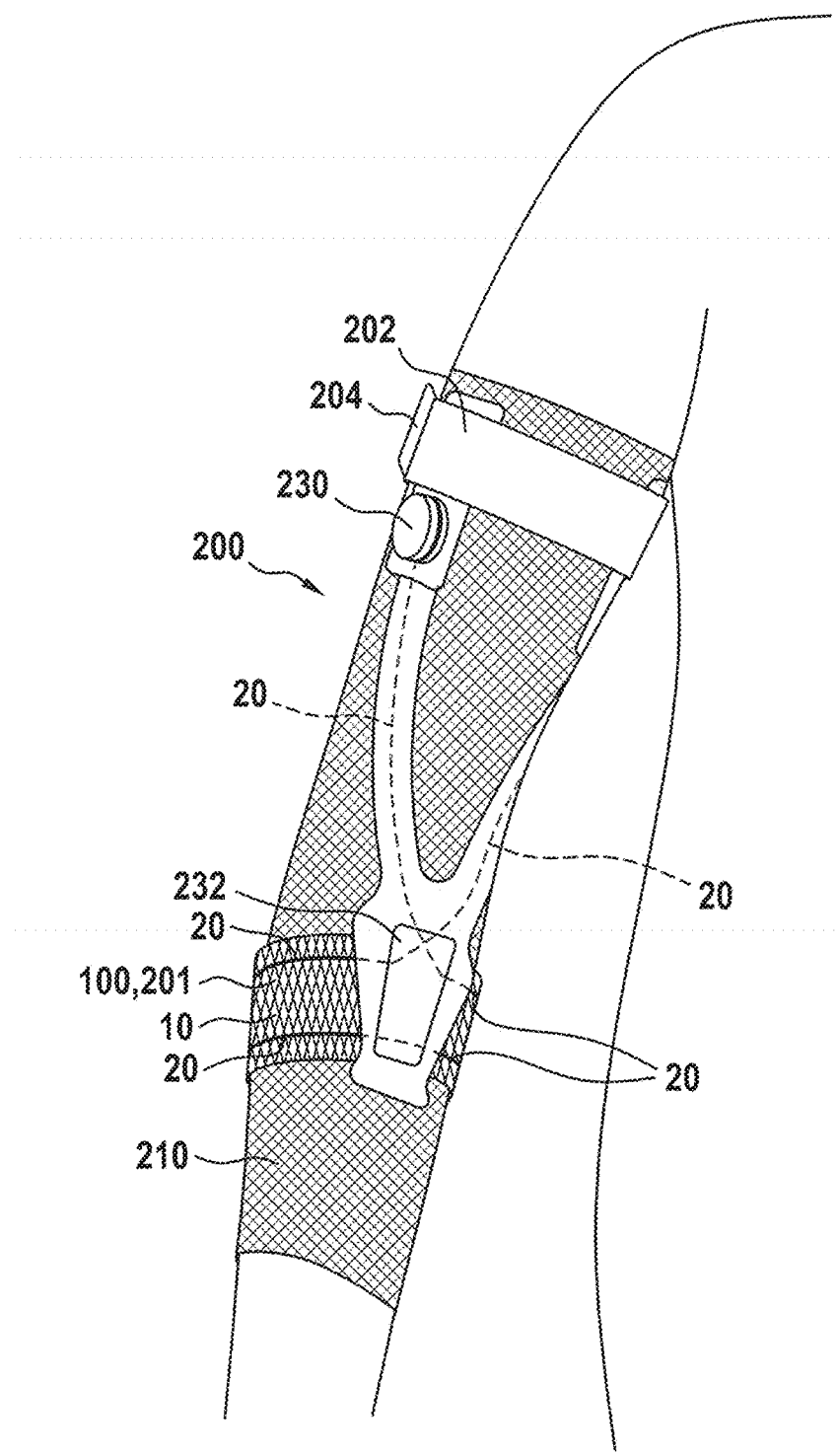
FIG. 6 an additional orthopedic aid with a tensioning strap according to the invention.

FIGS. 5 and 6 show examples of the use of the tensioning strap according to the invention (100) in orthopedic aids.

FIG. 5 shows a spinal orthosis (300). This is worn on the body with shoulder belts (60, 61). The shoulder belts (60, 61) must be tensioned so that the spinal orthosis (300) can act on the back. The belts (60, 61) are equipped with two tensioning straps (100) according to the invention. Each of the tensioning straps again has a strap-shaped base body (10), to which a pull cable (20) is assigned, as in FIG. 1. The pull cable exits from the strap-shaped base body (10) and runs along a belt section (60) of one of the belts (60, 61) in each case. At the end of the belt section (60), there is a roll-up element (50) with which the pull cable (20) can be rolled up. By rolling up the pull cable (20), the strap-shaped base body (10) contracts, whereby the shoulder belts (60, 61) are tensioned and pressed against the body, such that the spinal orthosis (300) can exert the desired pressure on the back. In order to once again relax the shoulder belts (60, 61) when the spinal orthosis (300) is removed, the roll-up element (50) can, for example, be decoupled, whereby the pull cable (20) can be unrolled from it once again. Due to the inherent rigidity of the band-like base body (10) and further optional structural properties, the band-like base body (10) can return to its relaxed original shape, enabling an easy repositioning and/or removal of the orthosis (300).

FIG. 6 shows an arm orthosis (200) with a tensioning strap (100) according to the invention. The tensioning strap (100) forms a cuff (201) that rests in a circular manner around the forearm. The cuff (201) is coupled to an abutment (202) encompassing the upper arm via a coupling element (232). The coupling element (232) serves to deflect the pull cable (20) in the direction of the abutment (202). However, the person skilled in the art can also provide alternative deflection elements. For example, a tensioning strap as shown in FIGS. 1 through 3 can reach completely around the forearm, wherein the two ends of the tensioning strap are connected to one another via an end element, and the end element serves to deflect the pull cable in the direction of the abutment. The abutment (202) has a roll-up element (230) into which the pull cable (20) of the tensioning strap (100) can be rolled up. This can generate a basic tension, by which the strap-shaped base body (10) is contracted and exerts a basic pressure on the underlying orthotic material (210), which is made as knitwear, and the forearm.

If the arm is stretched through, the path that the pull cable (20) spans from the cuff (201) to the abutment (202) is lengthened. This tensions the pull cable (20) even more, causing the strap-shaped base body (10) to contract even further and exert even more pressure on the forearm. The pressure now arising is so strong that further tensioning and thus overstretching of the arm is prevented. This is helpful, for example, in the training for throwing sports.

The invention claimed is:

1. A tensioning strap comprising a strap-shaped base body with a longitudinal direction, wherein the base body is compressible and/or extensible in the longitudinal direction, and comprising at least one pull cable, wherein the pull cable is fastened at one end of the base body and extends at least twice along the longitudinal direction of the base body, and wherein the pull cable is attached to a first end element of the base body and runs at least three times along the longitudinal direction of the base body, including an upper run, a lower run, and a middle run; wherein the upper run extends from the first end element along the longitudinal direction of the base body to a second end element and is deflected at the second end element; wherein the lower run extends from the second end element along the longitudinal direction of the base body to the first end element and is deflected at the first end element; and wherein the middle run extends from the first end element to the second end element along the longitudinal direction of the base body between the upper run and the lower run; and wherein the base body is designed as at least one of a netted strap and a mesh strap.

2. The tensioning strap according to claim 1, wherein the base body is compressible in the longitudinal direction.

3. The tensioning strap according to claim 1, wherein the tensioning strap is configured to tension a belt around a part of a user's body.

4. The tensioning strap according to claim 1, wherein the pull cable is deflected at at least one end of the base body.

5. The tensioning strap according to claim 1, wherein the tensioning strap is a component of at least one of an orthopedic aid, a medical aid, and a sports aid.

6. The tensioning strap according to claim 1, wherein the pull cable is formed as a pulley block.

7. The tensioning strap according to claim 1, wherein the pull cable is movably mounted in the base body.

8. The tensioning strap according to claim 1, wherein at least one of the netted strap and mesh strap is formed of plastic.

9. The tensioning strap according to claim 8, wherein at least one of the netted strap and mesh strap has a multiple number of recesses.

10. The tensioning strap according to claim 1, wherein a respective end element, which has a fastening device and/or a deflecting device for the pull cable, is assigned to the base body at its longitudinal direction ends.

11. The tensioning strap according to claim 1, wherein a roll-up element for tensioning and rolling up the pull cable is assigned to the base body at one longitudinal direction end.

12. The tensioning strap of claim 5, wherein the tensioning strap is the component the orthopedic aid, and wherein the orthopedic aid is an orthosis.

13. The tensioning strap according to claim 12, wherein the tensioning strap is designed to encompass a part of a user's body, which permits a circular closure of the tensioning strap.

14. The tensioning strap according to claim 13, wherein the orthosis is configured for cushioning or limiting joint movement of an extremity joint, having a cuff encompassing the extremity below the extremity joint, wherein the cuff is coupled to an abutment that can be applied to the extremity above the joint, wherein the pull cable extends from the abutment to the cuff and is connected in a force-fitting manner to the abutment and cuff wherein the cuff is assigned to the base body of the tensioning strap and the tensioning strap is formed as a pressure initiation section of the cuff, and wherein the pull cable is formed in such a manner that, in an applied state of the orthosis, it can be tensioned by the joint movement of the extremity, in order to thereby, via the tensioning strap exert compression on an underlying soft-tissue region of the extremity, in order to cushion or limit the joint movement.

15. The tensioning strap according to claim 14, wherein the pull cable can be tensioned in an area of the abutment by a roll-up element.

16. A tensioning strap comprising a strap-shaped base body with a longitudinal direction, wherein the base body is at least one of compressible and extensible in the longitudinal direction, the tensioning strap comprising a first end element attached at a first end of the strap-shaped base body and a second end element attached at a second end of the strap-shaped base body opposite the first end element, and at least one pull cable running contiguously at least three times through the longitudinal direction of the strap-shaped base body;

wherein the at least one pull cable passes through the longitudinal direction of the strap-shaped base body from the first end element to the second end element in a first pass, then from the second end element to the first end element in a second pass, and then from the first end element to the second end element in a third pass, wherein the third pass is extending longitudinally between the first pass and the second pass.

17. The tensioning strap of claim 16, wherein the at least one pull cable is removably attached to the first end element, and wherein the at least one pull cable may be pulled from the second end element.

18. A tensioning strap comprising a strap-shaped base body with a longitudinal direction, wherein the base body is compressible and/or extensible in the longitudinal direction, and comprising at least one pull cable, wherein the pull cable is attached to a first end element of the base body and runs at least three times along the longitudinal direction of the base body, including an upper run, a lower run, and a middle run; wherein the upper run extends from the first end element along the longitudinal direction of the base body to a second end element and is deflected at the second end element; wherein the lower run extends from the second end element along the longitudinal direction of the base body to the first end element and is deflected at the first end element; and wherein the middle run extends from the first end element to the second end element along the longitudinal direction of the base body between the upper run and the lower run; and wherein the base body is designed as at least one of a netted strap and a mesh strap.

* * * * *